United States Patent
McVey et al.

(10) Patent No.: US 6,982,029 B2
(45) Date of Patent: Jan. 3, 2006

(54) ELECTROPHORETIC METHOD AND SYSTEM HAVING INTERNAL LANE STANDARDS FOR COLOR CALIBRATION

(75) Inventors: Walter R. McVey, State College, PA (US); Thomas E. Kane, State College, PA (US)

(73) Assignee: SpectraMedix LLC, State College, PA (US)

( * ) Notice: Subject to any disclaimer, the term of this patent is extended or adjusted under 35 U.S.C. 154(b) by 840 days.

(21) Appl. No.: 09/849,239

(22) Filed: May 7, 2001

(65) Prior Publication Data

US 2002/0166767 A1    Nov. 14, 2002

(51) Int. Cl.
*B01D 59/42* (2006.01)
*C07K 1/26* (2006.01)

(52) U.S. Cl. .................. 204/461; 204/456; 204/450; 204/452

(58) Field of Classification Search ............... 204/450, 204/456, 461, 452
See application file for complete search history.

(56) References Cited

U.S. PATENT DOCUMENTS

| | | | |
|---|---|---|---|
| 5,789,153 A | * | 8/1998 | Falkner et al. .................. 435/5 |
| 6,013,444 A | | 1/2000 | Dau et al. ..................... 435/435 |
| 6,110,683 A | | 8/2000 | Reynolds et al. ............ 435/435 |

OTHER PUBLICATIONS

International Search Report of PCT/US/02/14002; filed May 2, 2002.

* cited by examiner

*Primary Examiner*—Ling-Sui Choi
(74) *Attorney, Agent, or Firm*—Fish & Richardson P.C.

(57) ABSTRACT

An electrophoretic system having a plurality of separation lanes is provided with an automatic color calibration feature in which each lane is separately calibrated. For each lane, a dye matrix standard is created using reference fragments which migrate either before, or after, the sample fragments being electrophoresced, during the same electrophoresis run. These dye standards are detected automatically for the purpose of determining coefficients used to identify sample fragments mixed together with the reference fragments. This allows for calibrating the dye standard matrix for each of a plurality of lanes each time the electrophoresis system is used.

15 Claims, 8 Drawing Sheets

Calibration Coefficients for each base

| Channel Number | G | A | T | C |
|---|---|---|---|---|
| 1 | .408 | .037 | .021 | .016 |
| 2 | 1 | .205 | .034 | .021 |
| 3 | .887 | .722 | .063 | .023 |
| 4 | .566 | 1 | .244 | .027 |
| 5 | .394 | .721 | .754 | .067 |
| 6 | .265 | .428 | 1 | .359 |
| 7 | .152 | .287 | .691 | .925 |
| 8 | .091 | .202 | .403 | 1 |
| 9 | .059 | .120 | .274 | .604 |
| 10 | .040 | .069 | .202 | .316 |

*Fig. 9*

ELECTROPHORETIC METHOD AND SYSTEM HAVING INTERNAL LANE STANDARDS FOR COLOR CALIBRATION

FIELD OF THE INVENTION

This invention is directed to electrophoresis equipment capable of identifying migrating species based on an analysis of detected fluorescence levels. More particularly, the present invention is directed to equipment capable of in-situ calibration in each separation lane. The inclusion of different reference fragments in a sample, having known lengths and known nucleotides associated with known dyes, allows for the calculation of a calibration matrix in each lane.

BACKGROUND OF THE INVENTION

Electrophoresis is a well-known technique for separating small amount of macromolecules. Increasingly, electrophoresis has become an indispensable tool for the biotechnology and other industries and is used extensively in a variety of applications, including the separation, identification and preparation of samples of nucleic acids, proteins and carbohydrates. Of increasing interest in the broader field of electrophoresis is capillary electrophoresis and electrophoresis on a microchip.

Capillary electrophoresis is gaining more popularity as a powerful separation technology. This is largely due to the impressive benefits that capillary electrophoresis provides, including the high-efficiency separation of large variety of compounds, such as amino acids, peptides, proteins, polymerase chain reaction (PCR) products, oligonucleotides, carbohydrates, vitamins, organic acids, polymers, chiral drugs, dyes, surfactants, and the like. Since capillaries have large surface area relative to their small volume, resulting in high cooling efficiency, high voltages can be applied in analyzing small quantities of samples at high speed and in high resolution. Capillary electrophoresis represents a separation platform that is highly suitable for massively multiplexing and efficiently automating most of the separations typically attained by labor-intensive slab gel electrophoresis to reduce the time required to obtain results from hours to minutes. Separated components are quickly identified by online detectors during the analysis, in contrast to the time-consuming staining steps required for slab gel separations. Current electrophoresis systems collect time domain data that indicate the presence of separated species.

For the present discussion, a "capillary" refers to any tube that can be used in capillary electrophoretic operations. Any capillaries suitable for performing capillary electrophoresis may be used in the present invention. These include, but are not limited to, fused silica capillary tubes. The tubes may have inner channel diameters in the range of about 20 to 1000 $\mu$m. Preferably, the inner channel diameters of these capillaries range from about 25 $\mu$m to 150 $\mu$m. Since capillaries have large surface area relative to their small volume, resulting in high cooling efficiency, high voltages can be applied in analyzing small quantities of samples at high speed and in high resolution.

One of the most important applications of electrophoresis systems is deoxyribonucleic acid (DNA) sequencing, in which the sequence of the four bases within a particular sample of DNA is determined. A conventional capillary array electrophoresis system is configured to perform a high-throughput analysis on biological samples, e.g., DNA sequencing, using a highly sensitive laser-induced fluorescence detection method.

In four-color fluorescent sequencing, each sample fragment is tagged with one of four fluorescent dyes, sometimes referred to as "tags". Each of the four tags preferentially binds to fragments terminating with one of four bases, i.e., guanine ("G"), adenosine ("A"), thymine ("T"), or cytosine ("C"). These samples are then excited with a laser beam, either while they are still migrating through the capillaries, i.e., on-column detection, or after they elute from output ends of the capillaries, i.e., sheath-flow detection, as described in U.S. Pat. No. 5,741,412 to Dovichi et al., causing the samples to emit fluorescence light. The emitted fluorescence light is detected as the tagged fragment migrates through a detection zone and subsequently analyzed. The identity of the fluorescent tag and the corresponding terminal base can be determined from the wavelength range of the fluorescence of the tag. The relative sizes of a series of fragments can be determined from the detection order because, in the absence of errors, smaller DNA fragments migrate faster and reach the detection zone prior to larger fragments. Accordingly, the sequence of bases in a DNA molecule can be determined from the fluorescence wavelengths of the tags bound to sequentially detected fragments.

It is known to then color separate these different dyes by the use of separate electrophoreses of reference DNA fragments containing the fluorescent dyes being used in the sample. For example, if an electrophoresis run uses four separate fluorescent dyes, one has to conduct four additional electrophoresis runs, one for each dye for calibration purposes. The data from these additional runs are used to obtain color calibration information, typically in the form of a calibration matrix which allows one to separate the contributions analyze the spectrum of fluoresced light resulting from the excitation of a species tagged with a particular a dye. The calibration matrix is then used for subsequent multiplex runs until the color separation ability is exhausted, or until a component of the system is altered rendering the calibration matrix invalid. This process can only be accomplished with the use of pure dye standards and requires dedicated tubes and wells for each of the dye standards, thus lowering efficiency, throughput, and accuracy.

Various attempts have been made to perform multiple capillary electrophoresis simultaneously. U.S. Pat. No. 6,027,627 to Li et al. discloses an automated capillary electrophoresis apparatus having a plurality of capillaries which are filled with migration medium and have first ends into which samples are injected and second ends from which components included in the samples are eluted.

Figure 1:
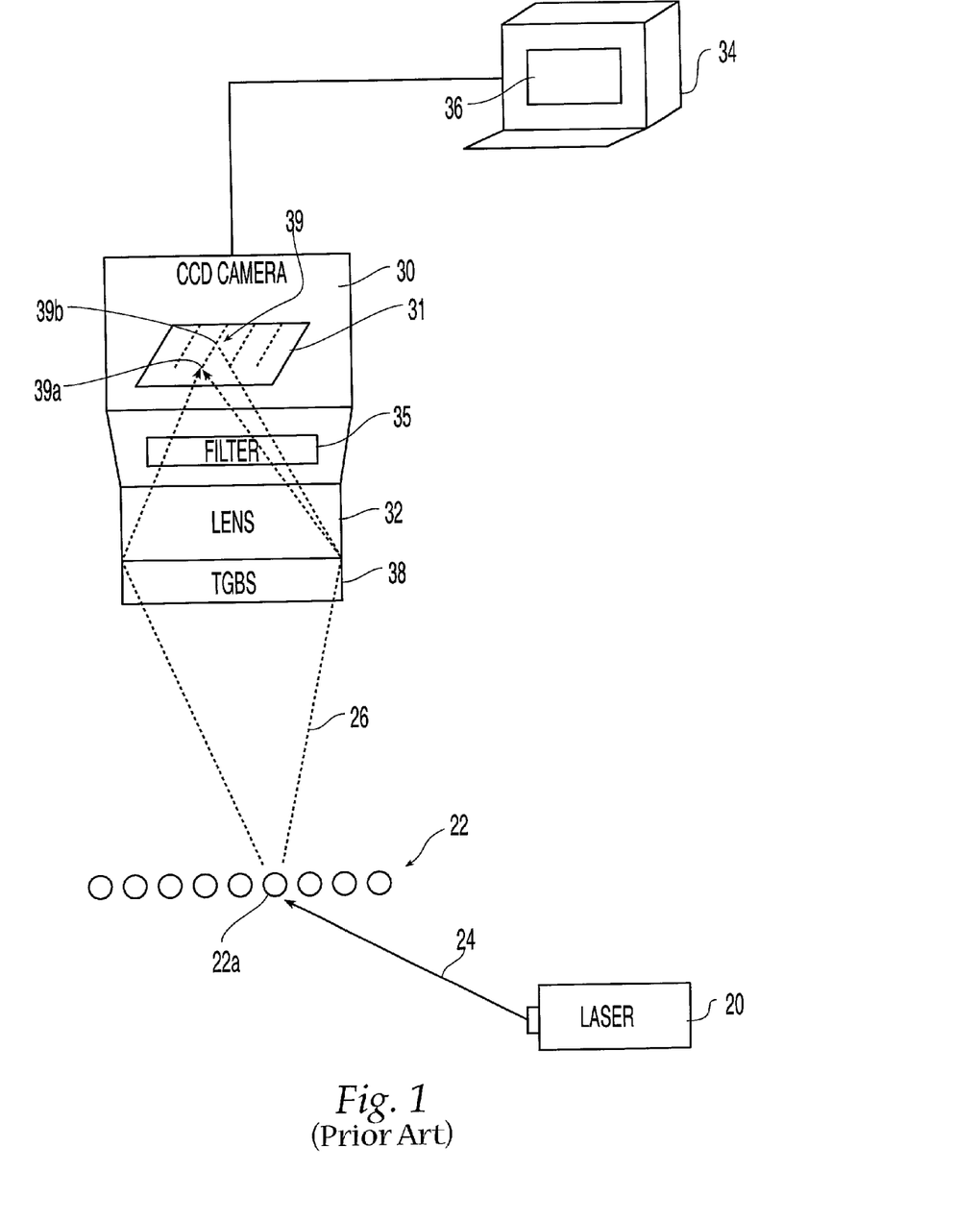
FIG. 1 shows a prior art detector system with a transmission grating beam splitter.

U.S. Pat. No. 5,998,796 to Li et al. discloses a detector system suitable for use with an electrophoretic apparatus. FIG. 1 illustrates the disclosed detector system. In this figure, a laser 20 emits a beam 24 of light which impinges on a plurality of capillaries 22 aligned parallel to one another. The light impinges on each capillary, causing tagged DNA fragments, or other tagged species, within each capillary 22a to fluoresce. The fluoresced light 26 passes through a transmission grating beam splitter 38, a lens 32 and a filter 35 before it is received on a CCD detector array 31 belonging to a camera 30. Light detected at the camera 30 is then sent on to a computer 34 where it may be viewed, in an appropriate form, on a display 36. The CCD detector array 31 preferably includes 1024×256 pixels. The first pixel dimension, (1024 pixels) includes 96 parallel capillaries, each capillary being focused onto at least one of the 1024 rows. The number of rows per capillary can be increased by selecting a lens with a different focal length or changing other optical parameters. In this system, a fluorescence spectrum, e.g., as represented by the $1^{st}$ order components, is created for each capillary and detected. The second pixel dimension (256 pixels) is focused on the spectrum spread by the transmission grating. The separated, fluoresced light from a given capillary 22a is detected by pixels of a particular column 39 of the array 31, with the 0th order component being detected by a first pixel 39a and the 1st order component being detected by at least one of a plurality of second pixels 39b spaced apart from the first pixel.

Figure 2A:
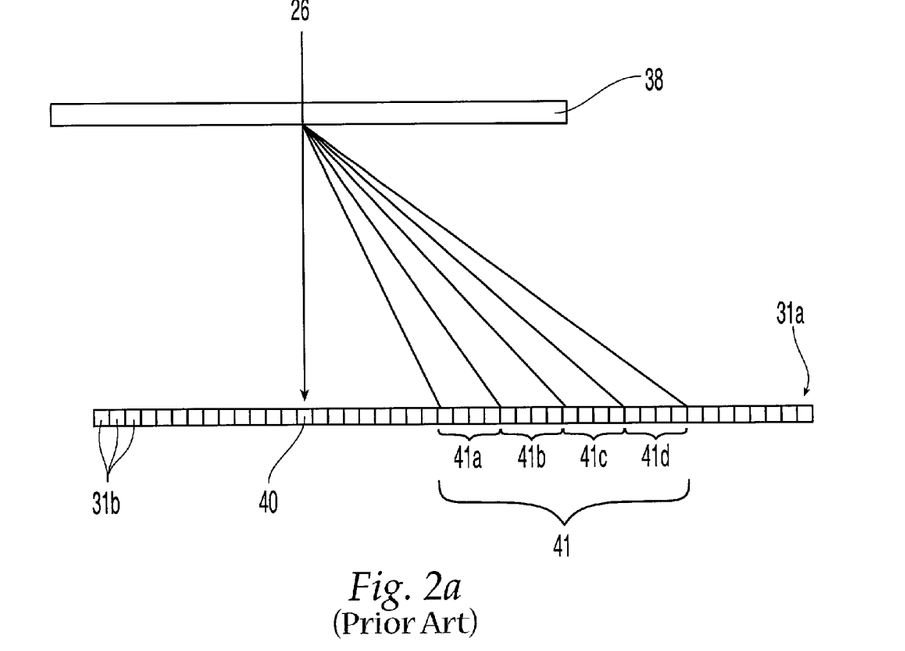
FIGS. 2a and 2b shows a prior art transmission grating beam splitter separating incoming light into $0^{th}$ and $1^{st}$ order spectral components.
Figure 2B:
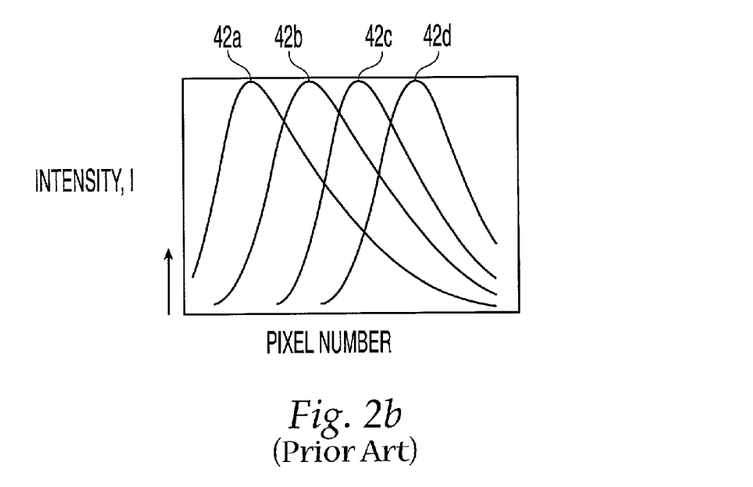

FIGS. 2a and 2b show the effect of a detector on incoming light 26 from tagged DNA samples of a single capillary. For simplicity, only the transmission grating beam splitter 38 and one pixel column 31a of the detector array 31, comprising a plurality of pixels 31b, is shown in FIG. 2a. The incoming light 26 is separated into a 0th order component 40 and a 1st order component 41. As shown in FIG. 2a, the 0th and 1st order components are spatially separated from each other, as they impinge on the pixel column 31a. This separation will subsequently allow one to use the intensities of both the 0th order and the 1st order transmitted incoming light components when performing subsequent analyses for identifying particular fluorophores, and hence, the corresponding nucleotides.

As is known to those skilled in the art of DNA sequencing using capillary electrophoresis, each of the four DNA nucleotides are typically tagged with one of four fluorophores which fluoresce in overlapping wavelengths. Thus, in FIG. 2a, the detected 1st order light 41 comprises four sub-bands, designated 41a, 41b, 41c, and 41d, each corresponding to a region along the column of pixels 31a, in which a particular one of the four fluorophores dominates.

FIG. 2b shows the relative intensity of fluorescence of the four fluorophores as a function of relative pixel number. Here, increasing pixel number corresponding to increasing wavelength. In FIG. 2b, curves 42a, 42b, 42c, and 42d correspond to the fluorescence emission spectra of the four fluorophores, each of which is shown to be dominant in a corresponding one of the four pixel regions 41a, 41b, 41c, and 41d of FIG. 2a.

As stated above, in FIG. 2a, the pixel column 31a corresponds to the detector output for a single capillary. For that one capillary, data is available for a number of contiguous pixels, including a small number of pixels which have 0th order information, and a larger number of pixels which have 1st order information. This offers some flexibility in performing subsequent analysis to determine exactly which fluorophore is present at any given time.

The spectrum of interest should include the wavelengths of light at which the dyes are known to fluoresce. The spectrum of interest for each capillary is spread over P contiguous pixels and these are divided into R channels of Q contiguous pixels, R=P/Q. For example, in a system with 30 contiguous pixels, there may be 10 channels of 3 contiguous pixels. R should be as large, preferably greater than, the number of dyes M being used.

The detector then outputs the spectrum having R light intensity values for each capillary and each time that data is fed to a processor. The processor then maps the spectrum of R intensity values for each capillary, onto values which help determine what dye has been detected in a specific capillary. This is typically done by multiplying color calibration coefficients by the vector of intensity values, for each capillary.

The principle behind the color calibration coefficients is that a spectrum of received light intensities in each of the channels is caused by the spectrum of a single dye (tagging a corresponding base) weighted by the effects (color calibration coefficients) of the detection system.

If $I_0(n), I_1(n), \ldots I_9(n)$ represent the measured intensities of the R=10 channels at the nth set of outputs from the CCD (after preprocessing including detection, binning, and baseline subtraction), $B_0(n), B_1(n), \ldots, B_3(n)$ is a vector representing the contribution (presence 1 or absence 0) from the M=4 bases, and Cij are coefficients of a known 10×4 matrix which maps the bases onto the detected channels, having the relationship of Equation 1:

$$\begin{pmatrix} I_0(n) \\ I_1(n) \\ I_2(n) \\ \ldots \\ \ldots \\ I_9(n) \end{pmatrix} = \begin{pmatrix} C_{00} & C_{01} & C_{02} & C_{03} \\ C_{10} & C_{11} & C_{12} & C_{13} \\ C_{20} & C_{21} & C_{22} & C_{23} \\ \ldots & \ldots & \ldots & \ldots \\ \ldots & \ldots & \ldots & \ldots \\ C_{90} & C_{91} & C_{92} & C_{93} \end{pmatrix} (B_0(n) \ B_1(n) \ B_2(n) \ B_3(n)) \quad (1)$$

Equation 1 can be rewritten as Equation 2:

$$I(n) = C\, B(n) \quad (2)$$

Given a vector of intensities output by a CCD for each separation lane, the theory of determining the presence or absence of each of the M=4 bases from the R=10 wavelength channels is fairly well established. This is simply a particular case of an over-determined system in which a smaller number of unknowns is determined from a greater number of equations. After mathematical transformation, Equation 2 can be written as Equation 3:

$$B(n) = (C^T C)^{-1} C^T I(n) \quad (3)$$

where $B_0(n), \ldots, B_2(n)$ now represent the unknown values of the individual bases as functions of time index n, each value being reflective of the relative likelihood of the corresponding dye tagging that base being present; $I_0(n), I_1(n), \ldots I_9(n)$ are the fluorescence intensities of the ten channels, and Cij's are the coefficients of wavelength i under known base j and where $C^T$ is a transpose of the matrix C and $A = (C^T C)^{-1} C^T$ is the pseudo-inverse of matrix C. While in the above analysis, C is a 10×4 matrix because a total of ten channels and four bases are used, in the general case, C is an R×M matrix wherein R≧M, and R and M are both integers greater than 2.

Typically, in prior art systems, the calibration matrix C is determined at the time the system is created. More particularly, the calibration matrix C is specific to a set of dyes used, and is constant for all separation lanes in a system. If such a prior art system is then modified, such as by upgrading to a new set of optical filters, the calibration matrix C needs to be re-calibrated.

One drawback of a constant calibration matrix is that the $0^{th}$ order and $1^{st}$ order spectral intensities from various capillaries in the capillary array do not fall on the same-positioned pixel as do the $0^{th}$ order and $1^{st}$ order spectral images from the remaining capillaries, but rather are offset by a skew of a single pixel or map onto more than one pixel. The binning process for $1^{st}$ order intensities for these abnormal capillaries results in a spectrum which would be slightly different than if the binning process started one pixel over.

In general, different dye sets have different spectra. As a consequence, each dye set has a different calibration matrix. Consequently, a further disadvantage of using a single calibration matrix for a multi-lane separation system, is that one cannot run multiple dye sets in different separation lanes. U.S. patent application Ser. No. 09/676,526, filed Oct. 2, 2000, provides a method and apparatus for a multi-lane electrophoretic separation apparatus that simultaneously utilizes multiple calibration matrices to calibrate for different dyes used to tag migrating species. Each calibration matrix is calculated "on the fly" based on the data received from that electrophoresis run.

SUMMARY OF THE INVENTION

The present invention creates color calibration information based on electrophoretic fluorescence data from groups of known-length dye-tagged reference fragments, which are combined with the dye-tagged sample fragments. Each group includes reference fragments having the same length, and each such reference fragment is tagged with the same dye. The length of reference fragments in one group differs from the length of reference fragments in a second group, and the lengths of the reference fragments in all groups differs from those of the sample fragments being analyzed. This results in all the reference fragments migrating either before, or after, the sample fragments, but in the same separation lane and during the same electrophoresis run. Since each group of known-length reference fragments is tagged with a single dye, one can determine color calibration information for that dye based on the spectral peaks in the detected fluorescence from reference fragments in that group. The color calibration information for each of the dyes can then be used to deconvolve detected fluorescence from the sample fragments.

The present invention is also directed to an electrophoretic method in which spectral fluorescence data from one portion of an electrophoresis run conducted in a separation lane is used to calculate color calibration information for use in deconvolving spectral fluorescence data from a second portion of the same electrophoresis run.

The present invention is also directed to an electrophoretic apparatus having an associated computer provided with a computer memory configured to store executable software code. The software code includes code for determining color calibration information from a first portion of spectral information obtained during an electrophoresis run, as well as code for identifying fluorescent species from a second portion of the spectral information obtained during the same electrophoresis run, based on the color calibration information obtained from the first portion of the spectral information.

The present invention is also directed to a computer-readable medium having executable software code stored thereon. The computer-readable medium includes code for determining color calibration information from a first portion of spectral information obtained during an electrophoresis run, as well as code for identifying fluorescent species from a second portion of the spectral information obtained during the same electrophoresis run, based on the color calibration information obtained from the first portion of the spectral information. The code is configured to obtain the first and second portions of spectral information from a single data source.

BRIEF DESCRIPTION OF THE DRAWINGS

The present invention is described with reference to the attached drawings in which.

DETAILED DESCRIPTION OF THE INVENTION

The contents of aforementioned U.S. Pat. Nos. 6,027,627 and 5,998,796, and U.S. patent application Ser. No. 09/676, 526 are incorporated by reference to the extent necessary to understand the present invention.

The present invention provides a novel method and apparatus to standardize which emission spectra is associated with which substance (fluorescent dye). The present invention is particularly useful when related to an apparatus and method for using reference fragments within the same electrophoretic run as the multiplexed PCR products, i.e., the sample DNA fragments. This eliminates the requirement of running additional dedicated electrophoresis runs for the sole purpose of identifying the emission spectra of the dye species in question. The invention advantageously has the capacity to run additional multiplexed runs with improved efficiency and improved color separation accuracy compared to prior art slab gel electrophoresis, capillary electrophoresis, and multiple capillary array electrophoresis systems.

In multiplexed PCR electrophoresis systems, there is typically a region where there are no PCR products migrating past the detector due to their size. This region can be classified as the time from the beginning of the electrophoresis until the PCR primers begin to migrate past the detector. This region provides a unique opportunity to have dye color standards, attached to reference fragments, migrate past the detector for the purpose of standardizing color spectra for the dye species in question. Additionally, there is a region after all the multiplex PCR products have migrated past the detector, which also provides an opportunity to have dye standards detected. In addition, there may be other non-PCR settings in which sample fragments to be electrophoresed are all with a certain range of lengths, thereby providing opportunities to run dye standards.

For illustrative purposes of PCR, the sample fragments can be controlled to be between about K1=200 and K2=350 base pairs in length, with each incremental length represented in the mix of fragments, i.e., 200, 201, 202, . . . , 350. For the present purposes, these are referred to as "sample fragments". This leaves ranges of lengths (lengths between 1 and K1-1) and (lengths greater than K2), referred to here as "blank regions", for which no sample fragments are being electrophoresced. The crux of the present invention focuses on these blank regions, providing a unique opportunity for in situ calibration in each separation lane. This blank region can be classified as the time from the beginning of the electrophoresis until the sample fragments between lengths K1 and K2 begin to migrate past the detector, using the above example, less than K1=200 base pairs in length, or as the time after the sample fragments have migrated past the detector, using the above example, greater than K2=350 base pairs in length. Though the present discussion uses particular values for K1 and K2, it is understood that K1 and K2 can assume other positive integer values, as well.

In the present invention, "reference fragments" having known lengths outside of the range of K1 to K2, are prepared and combined with the sample fragments into a common volume and both types of fragments are electrophoresed together in the same separation lane. Thus, the reference fragments may all be smaller in size than the sample fragments, or they may all be larger in size that the sample fragments. When the reference fragments are smaller in size than the sample fragments, they migrate first along the separation lane and are detected first. On the other hand, when the reference fragments are larger in size than the sample fragments, they migrate slower than the sample fragments and are detected after the sample fragments. While it is preferred that all the reference fragments be either larger than or smaller than, the sample fragments, the present invention also contemplates the possibility that some reference fragments are smaller than the sample fragments while others are larger than the sample fragments.

In the case of PCR products, the sample fragments include chains of four different nucleotides, i.e., G, A, T and C, the chains representing all lengths from K1 to K2. Each such chain is tagged with a dye $D_1$, $D_2$, $D_3$, and $D_4$ in a known manner, with the nucleotide in a particular position, e.g., the last nucleotide, determining which dye tags that chain. The reference fragments have known lengths $L_1$, $L_2$, $L_3$, and $L_4$, all outside the range of the sample lengths, and each having a different one of the four nucleotides in that particular position, are tagged with the same four dyes.

Figure 3:
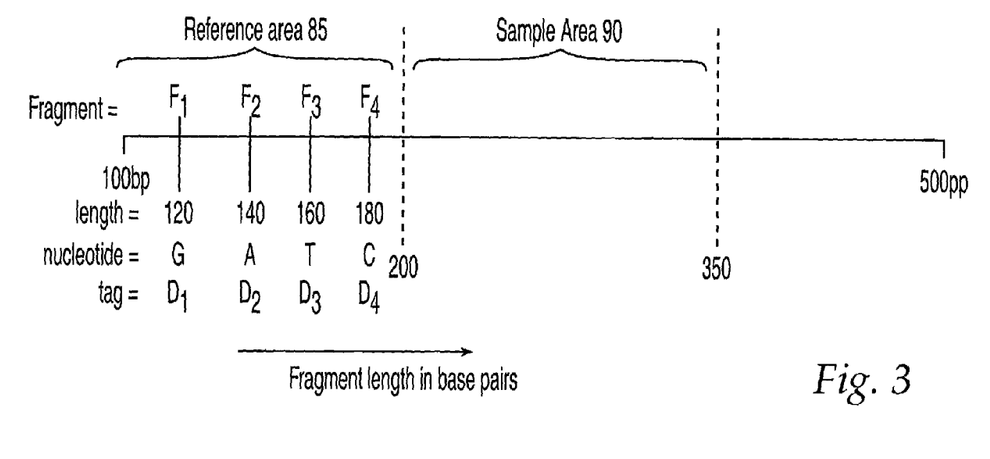
FIG. 3 illustrates the first and second portions of electrophoretic data in which the reference fragments are smaller than the sample fragments.

FIG. 3 shows the reference area 85, which targets the blank region before the sample area 90 (K1=200 to K2=350 base pairs). Four fragments, $F_1$, $F_2$, $F_3$, and $F_4$, have lengths 120, 140, 160, and 180, respectively, and are tagged with four members $D_1$, $D_2$, $D_3$, and $D_4$ of the chosen dye set, respectively, the dyes marking, in this example, nucleotides G, A, T, and C.

Figure 4:
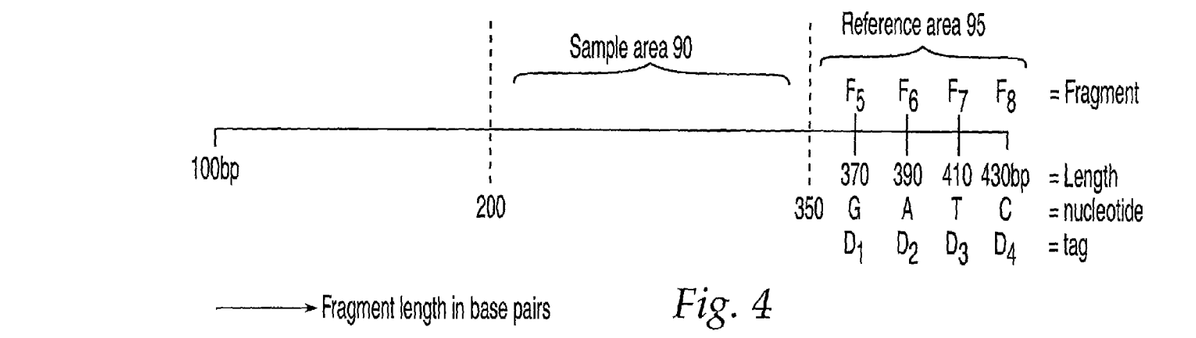
FIG. 4 illustrates the first and second portions of electrophoretic data in which the reference fragments are larger than the sample fragments.

FIG. 4 shows the reference area 95, which targets the blank region after the sample area 90 (K1=200 to K2=350 base pairs). Four fragments, $F_5$ of length 370, $F_6$ of length 390, $F_7$ of length 410, and $F_8$ of length 430 are tagged with the same four dyes $D_1$, $D_2$ $D_3$, and $D_4$, respectively, the dyes corresponding in this example to nucleotides G, A, T, and C.

The reference fragments then migrate past the detector, before (FIG. 3) or after (FIG. 4) the sample fragments and the data received from the reference fragments are used to standardize color spectra for each of the dyes used with the sample fragments. The dyes used must be covalently bound to a negatively charged organic molecule, organic polymer, biochemical polymer, or biochemical molecule, and the spectral properties of the detected references must be the same as the samples to be analyzed.

While in these examples, the length spacing between the reference fragments is identical (20 base pairs apart), it should be kept in mind that the lengths of the reference fragments may be unevenly spaced, or staggered. Thus, in FIG. 3, the reference fragments may have lengths $F_1$, $F_2$, $F_3$, and $F_4$, of 110, 125, 150, and 185, respectively. Such staggered spacing may be useful to help unambiguously identify a reference fragment, based on the relative lengths of its neighboring reference fragments.

The present invention is next described with reference to a detector system in which a total of P=30 pixels are binned into R=10 wavelength channels of Q=3 pixels each. The binning is done onboard the CCD array chip under software control. For DNA sequencing of PCR sample fragments, the number of dyes M is 4—one for each nucleotide—and the spectrum of interest, based on the chosen dye set, is in the range of 520 nm to 670 nm. Thus, the spectral resolution of the 10 wavelength channels is about 15 nm each. During data collection, for each of the 96 capillaries, 10 data points are offloaded each time the CCD array is read out and these values are stored for subsequent analysis. Furthermore, during an electrophoresis run, data from the CCD array is offloaded periodically, at a sample rate of f samples per second. Thus, during a run which lasts time T, a total of N=fT samples are taken. It is to be understood that the basic values presented above are for illustrative purposes only, and that the variables P, R, Q, and T, as well as other system parameters can be modified.

Figure 5:
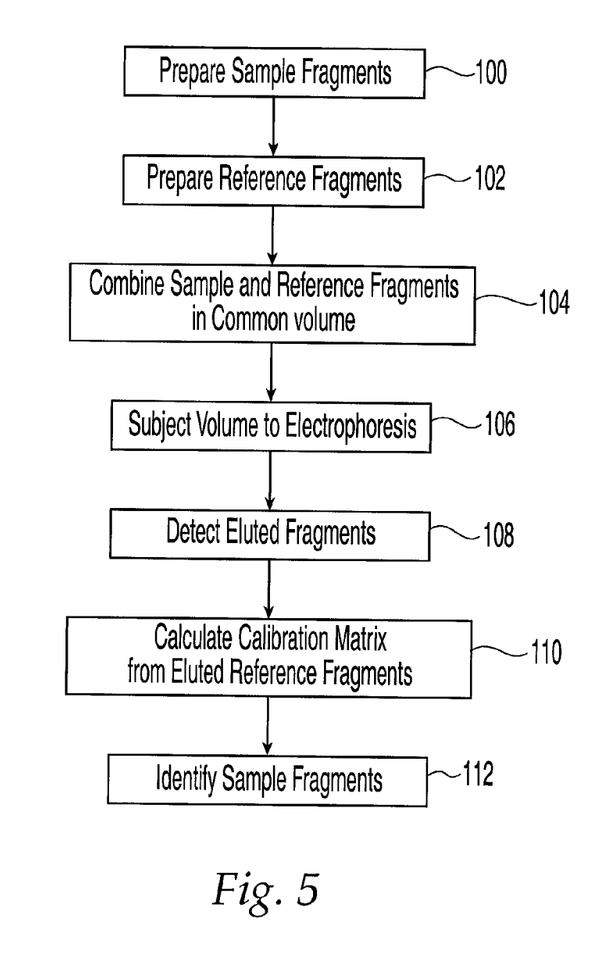
FIG. 5 shows a flow chart outlining the steps according to the invention.

FIG. 5 illustrates the general sequence of events according to the invention. A PCR process and other common techniques are carried out on a DNA sample (Step 100), resulting in sample fragments of all possible lengths between K1=200 and K2=350. The sample fragments are then exposed to a fluorescent dye set, with the terminal nucleotide of each fragment being covalently bound to a fluorescent dye. A plurality of reference fragments are prepared (Step 102), as described above. The reference fragments and sample fragments are then combined into a common volume (Step 104).

The common volume is subjected to capillary electrophoresis (Step 106). For this, a high voltage is applied across the capillary to separate molecules based on differences in charge-to-size ratio. Differences in the migration rates causes the fragments to separate into bands of similar-length fragments. As the bands traverse the capillary channel, the bands are irradiated, causing the fragments to fluoresce, and the fluoresced light is detected at distinct time points using a detector (Step 108).

Figure 6:
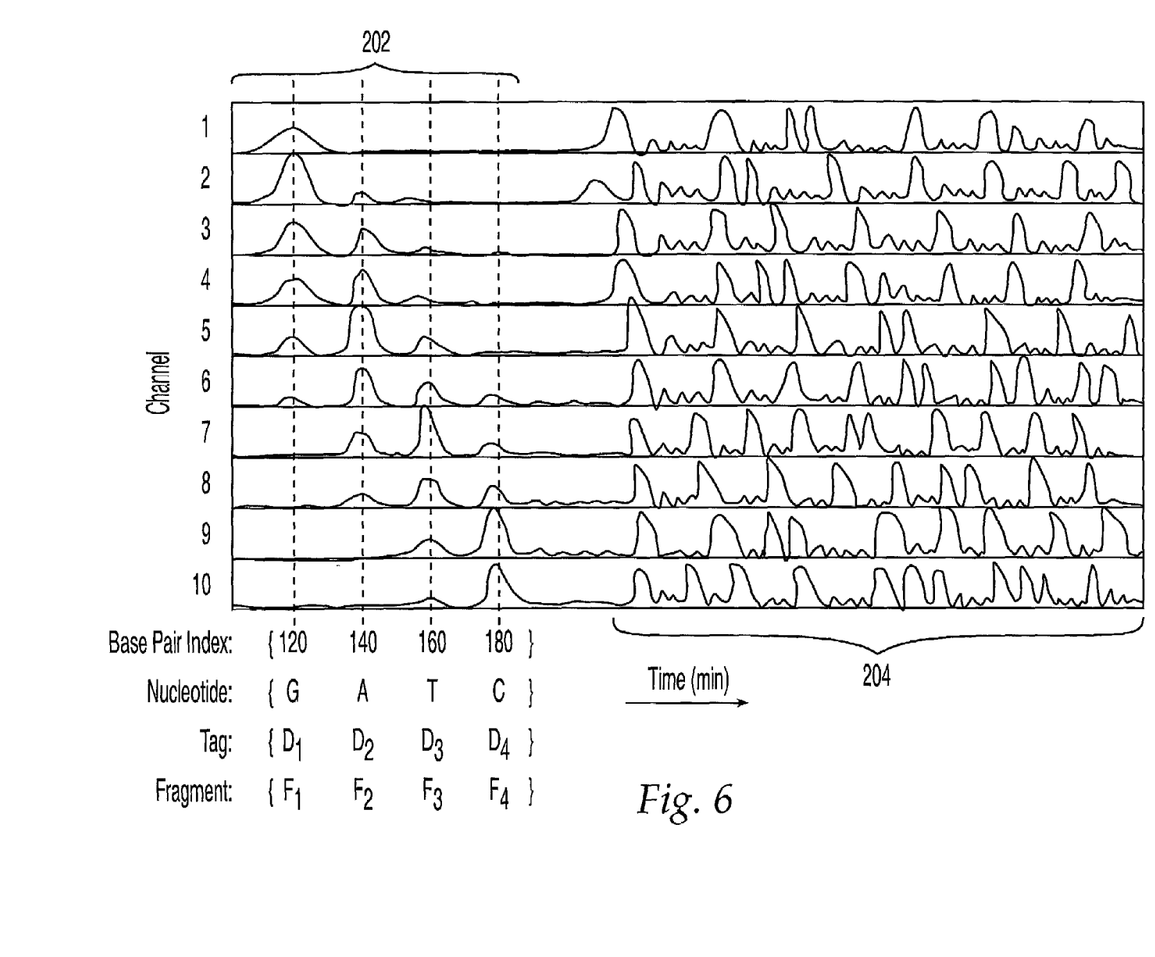
FIG. 6 shows synthetic data for intensity detected over 10 channels in accordance with the embodiment shown in FIG. 3.

As discussed above, and illustrated in FIGS. 1, 2a, and 2b, the fluoresced light from each capillary is separated into its spectrum, and the spectrum of light is received in a plurality of channels, each channel representing light energy collected at a different frequency or narrow range of frequencies. FIG. 6 shows synthetic results for the case in which reference fragments are smaller than the sample fragments and FIG. 7 shows synthetic results for the case in which the reference fragments are larger than the sample fragments.

Figure 7:
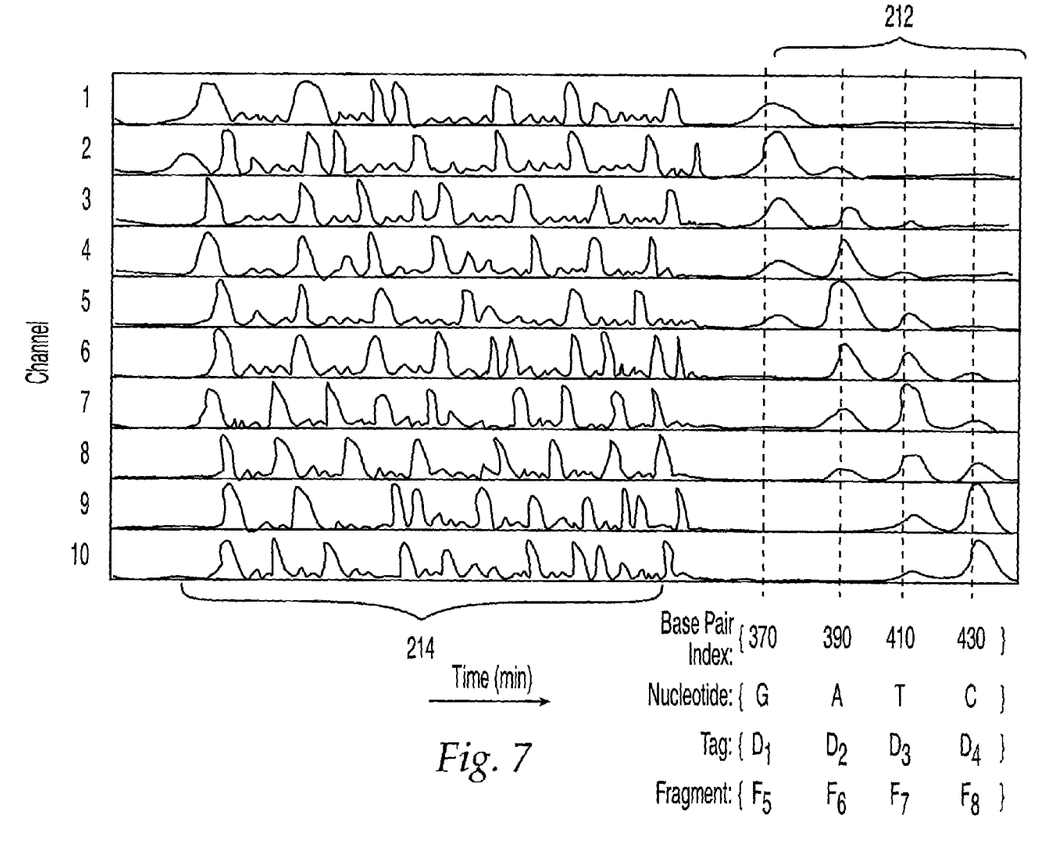
FIG. 7 shows synthetic data for intensity detected over 10 channels in accordance with the embodiment shown in FIG. 4.

Both FIGS. 6 and 7 show the relative light intensity received in each of 10 spectral channels as a function of time, with peaks along the time axis of any one channel corresponding to a band. At any one point in time, a plurality of channels exhibit peaks, due to the spectral nature of each of the dyes, as seen in FIG. 2b. In FIG. 6, however, the reference fragment region 202 precedes the sample region 204, while in FIG. 7, the reference fragment region 212 elutes after the sample region 214. These figures are explained with reference to FIG. 6, it being understood that FIG. 7 can be explained in a substantially similar manner.

In FIG. 6, the reference fragment region 202 shows the arrival of four distinct bands of fragments F1, F2, F3, and F4, which are spaced apart from each other in time. The nominal base pair indices for these are lengths 102, 140, 160, and 180, respectively. The four bands in the reference fragment region correspond the four dyes D1, D2, D3, and D4, respectively, each of which was attached to reference fragments of a particular length. Since there are preferably no fragments in the reference fragment region having lengths other than these, each band in the reference region corresponds to a single dye being attached to fragments of an identical length. In other words, the four bands in the reference region are caused by four groups of identical-length reference fragments, fragments within a group being tagged by a single dye.

As seen in FIG. 6, each band exhibits spectral energy over a plurality of adjacent channels, with the various bands exhibiting $1^{st}$ order spectral energy over different, overlapping sets of channels, much as seen in FIG. 2b. Since the distribution of spectral energy over the 10 channels for any one band is caused by a single dye which tags reference fragments having substantially identical lengths, one may use the normalized distribution as being representative of the color calibration coefficients over the 10 channels for that particular dye. The collection of color calibration coefficients for all four dyes can then be used to directly form the calibration matrix C. This calibration matrix can then be used to identify the dyes, and thus the corresponding nucleotides, which created the peaks in the sample region 204.

Figure 8:
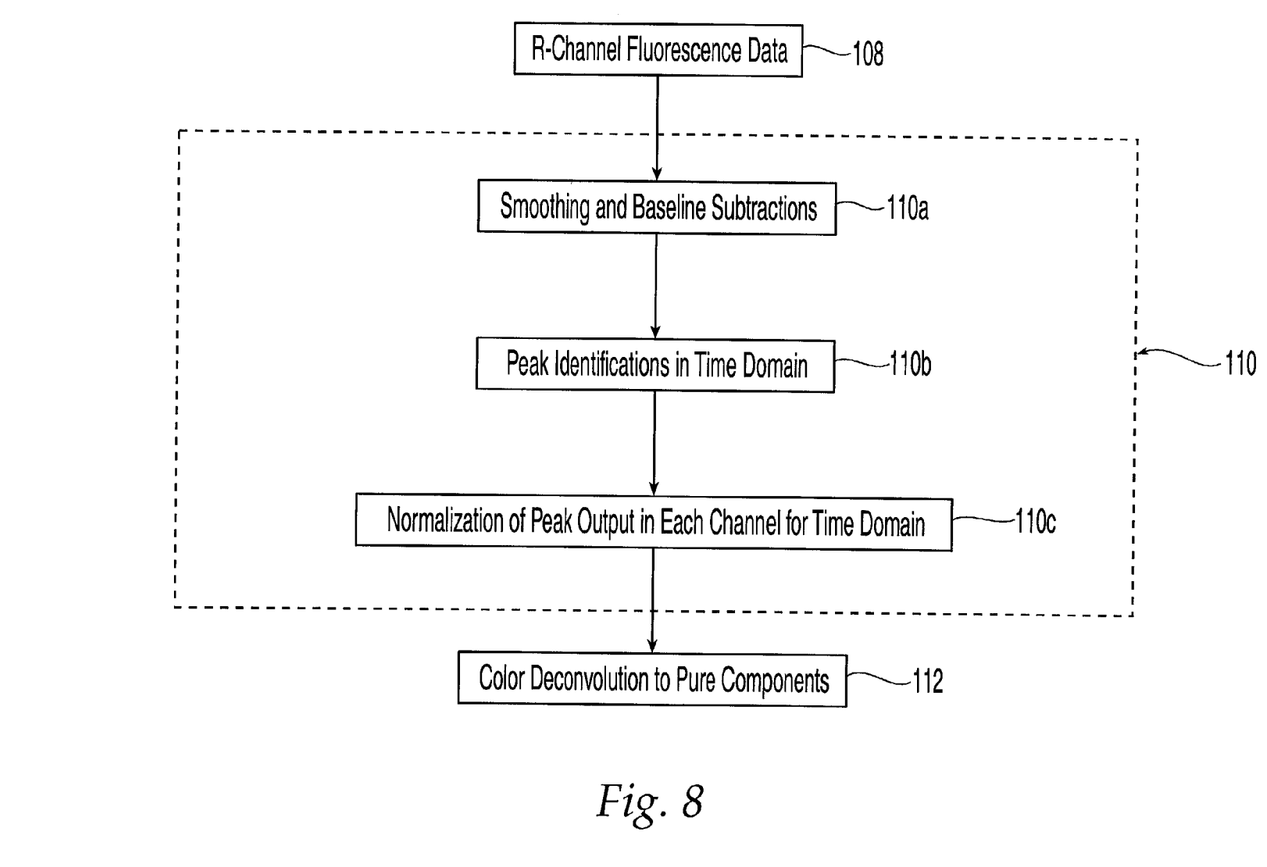
FIG. 8 shows a flow chart outlining the steps to create a calibration matrix in accordance with the invention.
Figure 9:
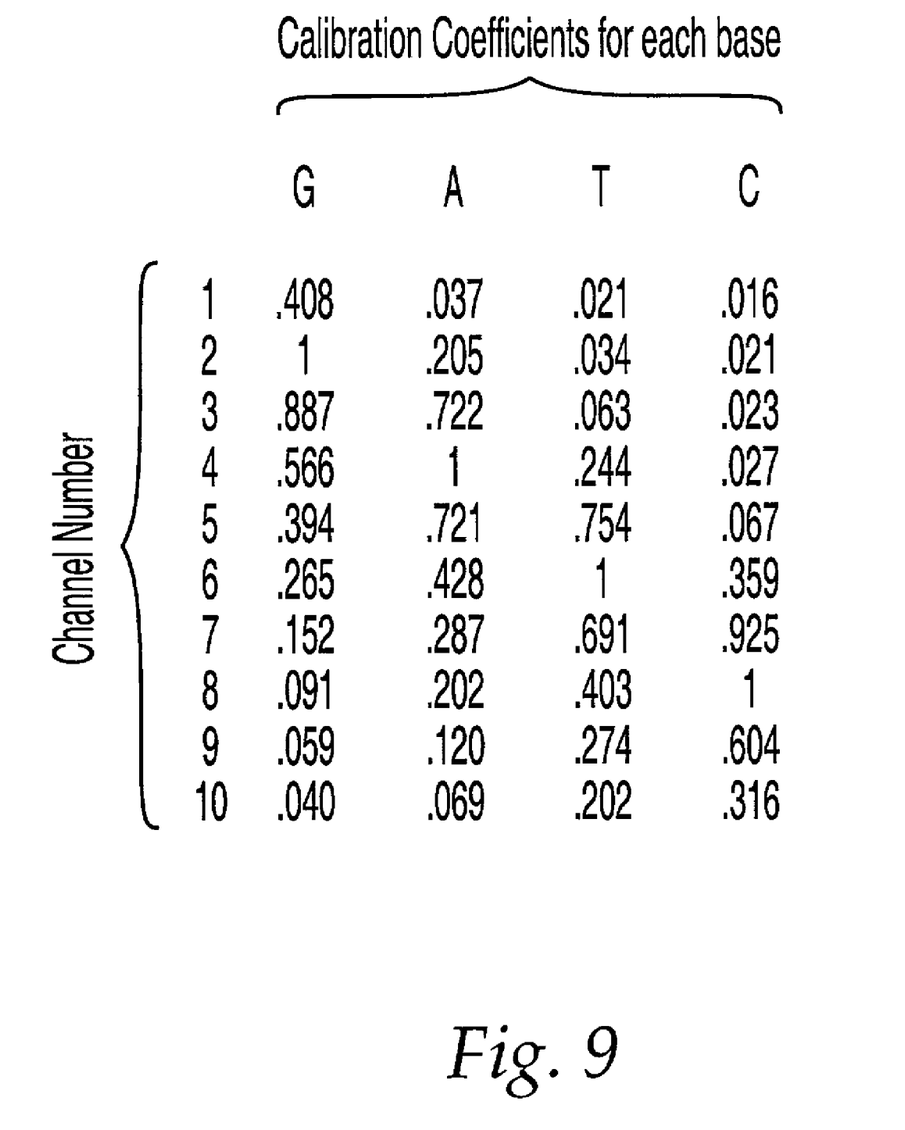
FIG. 9 shows a sample color calibration coefficient matrix in accordance with the invention.

FIG. 8 presents the process (110) for calculating the calibration matrix from the reference fragments detected in the reference region 202 After the electrophoresis data has been collected (Step 108), the data is subject to smoothing and baseline subtractions (Step 110a) Then, peaks across all 10 channels are identified in the reference region by first looking for the highest signal intensity at each point in time in the vicinity of where a reference fragment is expected to have been detected (Step 110b). Once such a local (in time) peak is found in some channel 'x' at some time point 't', the signal intensity values at time point 't' for the other 9 channels are normalized relative to the signal intensity value for channel 'x' at time 't' to thereby arrive at a calibration vector for the dye associated with that reference fragment (Step 110c). This process is repeated in the vicinity of where the other reference fragments are expected until peaks associated with all such fragments have been detected. In the preferred embodiment of four reference fragments, the above process results in four calibration vectors, one vector for each dye, with each calibration vector having values that range from 0.0–1.0. The assemblage of all four vectors results in a 10×4 calibration matrix, such as that shown in FIG. 9.

Once all four calibration vectors (and thus the calibration matrix C) have been establish, the final step is peak deconvolution (Step 112). Deconvolution requires the pseudo-inverse of color calibration coefficient matrix C to be calculated for each separation lane, which is then used to map a detected set of intensities from that separation lane, onto a decision vector B, as given in Equation 3. The position of the highest value in the decision vector B corresponds to the identity of the dye, from which the corresponding reference fragment's terminal nucleotide can be determined.

It is understood that the foregoing description of creating color calibration information is preferably implemented in software which resides in a computer memory associated with a computer to which the detector is connected. The memory may take the form of any one of well-known forms, such as a hard disk, an optical disk, CD-ROM, random access memories of various sorts (DRAM, SDRAM, etc.), read-only memories, flash memories, and so forth. The software may, of course, be stored and transported in a computer-readable medium such as a floppy-disk, CD-ROM, optical disk, or the like, which may make it amenable to be installed as a plug-in or upgrade to enhance existing software running on a computer associated with electrophoretic analysis.

The detected light is converted into electrical signals and these are offloaded to a computer memory for further processing. In general, the offloaded data from both the reference fragments and the sample fragments is placed in a single data file for later processing, or is received in a single data stream that is then processed by the computer "on the fly". Whether the processing is performed in real time, or offline, the software code is preferably configured to obtain the first and second portions of spectral information from a single data source, i.e., a single file, or a single data stream arriving at a designated port.

It is to be understood that the invention is not to be limited to the exact configuration as illustrated and described herein. For example, the present invention has applicability in slab gel electrophoresis, capillary electrophoresis, and multiple capillary array electrophoresis systems, among others. The embodiments discussed in the Detailed Description of the Invention are not intended to limit the invention. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method for performing electrophoresis comprising:
providing a plurality of sample fragments collectively having a first range of sizes, each of the sample fragments being tagged with a dye selected from a first group of dyes, a fluorescence spectrum of the dye of each sample fragment being indicative of a property of that sample fragment;
providing a plurality of reference fragments collectively having a second range of sizes which does not overlap with the first range of sizes, each reference fragment being tagged with a dye selected from the first group of dyes, reference fragments of substantially similar size being tagged with a common dye;
combining the sample fragments and the reference fragments into a common volume;
causing the sample fragments and the reference fragments within the common volume to separate along a common separation lane such that the sample fragments and the reference fragments are separated from one another in at least one of time and space;
optically detecting a fluorescence spectrum comprising a respective fluorescence intensity at each of a plurality of wavelengths from each of the separated sample and reference fragments;
determining first color calibration information based upon the fluorescence spectra of the reference fragments; and
determining at least one property of the sample fragments based upon the first color calibration information and the fluorescence spectra of the sample fragments.

2. The method according to claim 1, wherein the first and second ranges of sizes correspond to first and second ranges of lengths of the sample and reference fragments.

3. The method according to claim 2, wherein the sample and reference fragments comprises sequences of nucleotides.

4. The method according to claim 1, wherein the plurality of reference fragments comprise a first number of groups of reference fragments, reference fragments within each group having a substantially similar size.

5. The method according to claim 4, wherein the reference fragments comprise a sequence of nucleotides.

6. The method according to claim 5, wherein the reference fragments within each group comprises nucleotides having identical lengths.

7. The method according to claim 6, wherein the lengths of reference fragments within the groups are unevenly spaced.

8. The method according to claim 5, wherein lengths of nucleotides in any one group differ from lengths of nucleotides in any other group by at least five nucleotides.

9. The method according to claim 5, wherein lengths of nucleotides in any one group differ from lengths of nucleotides in any other group by at least ten nucleotides.

10. The method according to claim 5, wherein lengths of nucleotides in any one group differ from lengths of nucleotides in any other group by at-least twenty nucleotides.

11. The method according to claim 5, wherein lengths of nucleotides in any one group differ from lengths of nucleotides in any other group by at least forty nucleotides.

12. The method according to claim 1, wherein the largest sample fragment is smaller than the smallest reference fragment.

13. The method according to claim 1, wherein the largest reference fragment is smaller than the smallest sample fragment.

14. The method according to claim 1, wherein the first color calibration information is calculated for each of a plurality of separation lanes.

15. A method for performing electrophoresis comprising:
providing a plurality of sample fragments collectively having a first range of sizes, each of the sample fragments being tagged with a dye selected from a first group of dyes, a fluorescence spectrum of the dye of each sample fragment being indicative of a property of that sample fragment;
providing a plurality of reference fragments collectively having a second range of sizes which does not overlap with the first range of sizes, each of at least some reference fragments of different size being tagged with a dye selected from the first group of dyes, the fluorescence spectrum of the dyes of the different sized reference fragments being different;
combining the sample fragments and the reference fragments into a common volume;
causing the sample fragments and the reference fragments within the common volume to separate along a common separation lane such that the sample fragments and the reference fragments are separated from one another;
optically detecting a fluorescence spectrum comprising a respective fluorescence intensity at each of a plurality of wavelengths from each of the separated sample and reference fragments;
determining first color calibration information based upon the fluorescence spectra of the reference fragments; and
determining at least one property of the sample fragments based upon the first color calibration information and the fluorescence spectra of the sample fragments.

* * * * *